(12) United States Patent
Zhao et al.

(10) Patent No.: US 12,268,778 B2
(45) Date of Patent: Apr. 8, 2025

(54) BIFUNCTIONAL NUCLEOSIDE HYDROGEL, PREPARATION METHOD THEREFOR AND USE THEREOF

(71) Applicant: SICHUAN UNIVERSITY, Sichuan (CN)

(72) Inventors: Hang Zhao, Sichuan (CN); Xin Zeng, Sichuan (CN); Ning Ji, Sichuan (CN); Hui Feng, Sichuan (CN); Jiang Liu, Sichuan (CN); Qianming Chen, Sichuan (CN)

(73) Assignee: SICHUAN UNIVERSITY, Sichuan (CN)

( * ) Notice: Subject to any disclaimer, the term of this patent is extended or adjusted under 35 U.S.C. 154(b) by 820 days.

(21) Appl. No.: 17/594,657

(22) PCT Filed: May 31, 2019

(86) PCT No.: PCT/CN2019/089636
§ 371 (c)(1),
(2) Date: Oct. 25, 2021

(87) PCT Pub. No.: WO2020/215446
PCT Pub. Date: Oct. 29, 2020

(65) Prior Publication Data
US 2022/0218605 A1    Jul. 14, 2022

(30) Foreign Application Priority Data

Apr. 25, 2019    (CN) .......................... 201910340339.9

(51) Int. Cl.
| | |
|---|---|
| *A61K 9/06* | (2006.01) |
| *A61K 47/24* | (2006.01) |
| *A61P 35/00* | (2006.01) |
| *C07H 23/00* | (2006.01) |

(52) U.S. Cl.
CPC ................ *A61K 9/06* (2013.01); *A61K 47/24* (2013.01); *A61P 35/00* (2018.01); *C07H 23/00* (2013.01)

(58) Field of Classification Search
CPC ...... A61K 47/24; A61K 47/34; A61K 9/0019; A61K 9/06; A61P 35/00; C07H 23/00
See application file for complete search history.

(56) References Cited

FOREIGN PATENT DOCUMENTS

KR    100204309 B1    6/1999

OTHER PUBLICATIONS

Hang (Biomaterials (2020), 230, 119598.*
Peters, Gretchen Marie et al.; G4-Quartet M+ Borate Hydrogels, J. Am. Chem. Soc, vol. 137, Apr. 14, 2015, pp. 5819-5827.
Venkatesh, V. et al.; supramolecular Photocatiovatable Anticancer Hydrogels, J. Am. Chem. Soc, vol. 139, Apr. 17, 2017, pp. 5656-5659.
Tang, Fan et al.; Developing a Self-Healing supromolecular Nucleoside Hydrogel Based on Guanosine and Isoguanosine, Chem. Asian J., vol. 13, Jul. 4, 2018. pp. 1962-1971.
Zhao, Hao et al.; Self-Assembling Monomeric Nucleoside Molecular Nanoparticles Loaded with 5-FU enhancing Therapeutic Efficacy against Oral Cancer, ACS NANO, vol. 9, No. 10, Sep. 8, 2015, pp. 9638-9651.

* cited by examiner

*Primary Examiner* — Pancham Bakshi
(74) *Attorney, Agent, or Firm* — NKL Law; Allen Xue

(57) ABSTRACT

A bifunctional nucleoside hydrogel is formed by dissolving isoguanosine, guanosine and a borate in water or an aqueous solution and then crosslinking same. The bifunctional nucleoside hydrogel integrates a carrier and a drug effect and has a significant inhibitory effect on the activity of tumor cells, and in particular has a significant inhibitory effect on the activity of cells related to lung cancer, glioma, osteoma, colon cancer, breast cancer, oral squamous cell carcinoma and tongue squamous cell carcinoma, of which the inhibitory effect on the activity of cells related to oral squamous cell carcinoma is the best. Therefore, the bifunctional nucleoside hydrogel has potential application prospects in preparing anti-tumor drugs, and particularly, same can provide a new approach for treating oral squamous cell carcinoma.

17 Claims, 6 Drawing Sheets

BIFUNCTIONAL NUCLEOSIDE HYDROGEL, PREPARATION METHOD THEREFOR AND USE THEREOF

TECHNICAL FIELD

The present invention belongs to the field of biomedical materials, and in particular to a bifunctional nucleoside hydrogel as well as a preparative method and a use thereof.

BACKGROUND ART

In clinical, most patients with malignant tumors are in the middle and advanced stage at the time of treatment, and chemotherapy is one of the main means of comprehensive treatment. However, due to the low bioavailability, high toxic and side effects, drug resistance and other defects of traditional chemotherapeutic drugs, their wide clinical application is seriously limited. In order to overcome the defects of these drugs, the hydrogel drug delivery system is applied. Among them, supramolecular hydrogels formed by self-assembly of natural products and their derivatives have attracted widespread attention in drug delivery and cancer treatment because of their good biocompatibility, high loading capacity, site directed release, good sustained release and controlled release effects, and the similar. However, at present, most supramolecular hydrogels can only transfer drugs as carriers, and do not have anti-tumor activity in themselves. While some natural products have anti-tumor activity, however, because of their poor self-assembly properties, it is difficult to form hydrogels as delivery systems. Therefore, constructing a bifunctional supramolecular hydrogel with both carrier and therapeutic effects as well as studying its use in tumor therapy is of great scientific value and potential clinical significance.

CONTENT OF THE INVENTION

In order to solve the above problems, the present invention provides a bifunctional nucleoside hydrogel as well as a preparative method and a use thereof.

The present invention provides a bifunctional nucleoside hydrogel, that is formed by cross-linking of isoguanosine, guanosine and borate in water or aqueous solution.

Further, the molar ratio of isoguanosine, guanosine and borate is 1:(1-5):(1-5); preferably, the molar ratio of isoguanosine, guaniosine and borate is 1:1:1.

Further, in the mixed solution that is obtained by dissolving isoguanosine, guanosine and borate in water or in aqueous solution, the concentration of isoguanosine is 0.005-5.6 wt %; preferably, the concentration of isoguanosine is 0.3-5.6 wt %; more preferably, the concentration of isoguanosine is 1.4 wt %.

Further, said borate is selected from $LiB(OH)_4$, $NaB(OH)_4$, $KB(OH)_4$, $RbB(OH)_4$ or $CsB(OH)_4$; preferably, said borate is $NaB(OH)_4$.

Further, said water or aqueous solution is ultrapure water or phosphate buffer.

Further, said cross-linking after isoguanosine, guanosine and borate are dissolved in water or aqueous solution means that isoguanosine, guanosine and borate are dissolved in hot water or aqueous solution, followed by cooling and cross-linking.

Further, said cross-linking after isoguanosine, guanosine and borate are dissolved in water or aqueous solution means that isoguanosine and borate are added in water or aqueous solution and then allowed to dissolve under heating, to which is added guanosine and dissolved under heating, and the mixture is gradually cooled at room temperature and crosslinks.

The present invention provides a preparative method of the bifunctional nucleoside hydrogel mentioned above, that includes the following steps:

Isoguanosine, guanosine and borate are dissolved in water or aqueous solution under heating, and then cooled and crosslink.

Further, the preparative method mentioned above includes the following steps:

Isoguanosine and borate are added in water or aqueous solution, and then allowed to dissolve under heating, to which is added guanosine and dissolved under heating, and the mixture is gradually cooled at room temperature and crosslinks.

The present invention provides the use of the bifunctional nucleoside hydrogel mentioned above in the preparation of antitumor drugs; preferably, the tumors are lung cancer, glioma, osteoma, colon cancer, breast cancer, oral squamous cell carcinoma and tongue squamous cell carcinoma; more preferably, the tumors are oral squamous cell carcinoma.

The bifunctional nucleoside hydrogel of the present invention has both carrier and medicinal effects, as well as obvious inhibition on the activity of tumor cells, especially for lung cancer, glioma, bone tumor, colon cancer, breast cancer, oral squamous cell carcinoma, and tongue squamous cell carcinoma. Among them, the inhibition effect on the activity of oral squamous carcinoma cells is the best. In addition, the bifunctional nucleoside hydrogel of the present invention can inhibit the proliferation of transplanted tumor of oral squamous cell carcinoma HSC-3 cell lines in vivo. Therefore, the bifunctional nucleoside hydrogel has potential application prospect in the preparation of antitumor drugs. Especially, it can provide a new way for the treatment of oral squamous cell carcinoma.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

1. Key Raw Materials and Reagents of the Present Invention

Isoguanosine (analytically pure, Sinopharm): the structural formula is

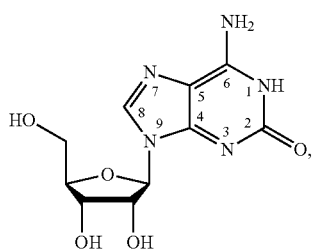

Guanosine (analytically pure, Sinopharm):

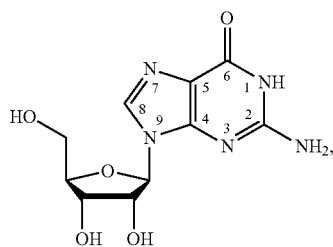

NaB(OH)$_4$ (analytically pure, Sinopharm), H$_2$O (Ultra pure water made in laboratory).

Figure 1:
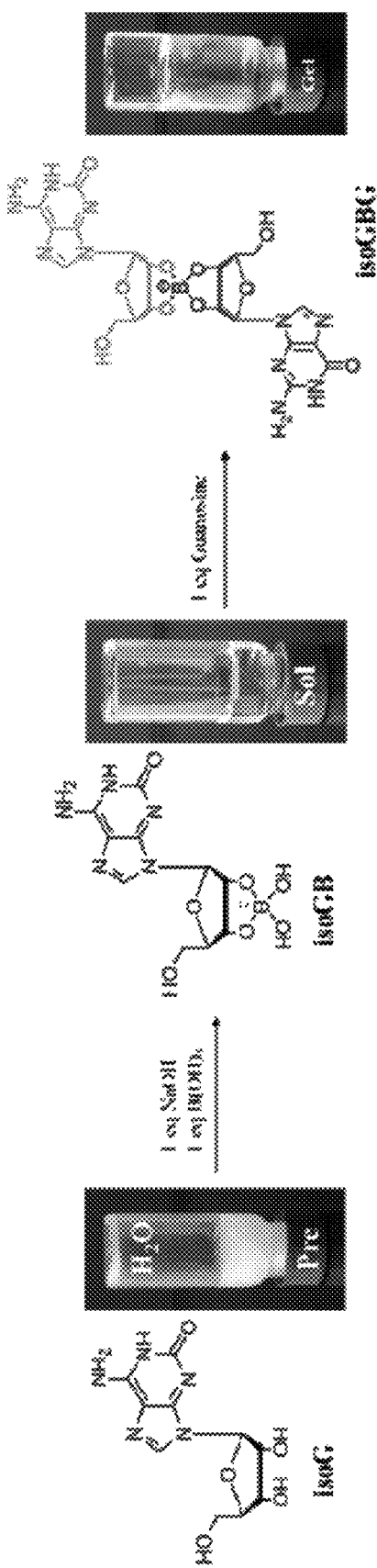
FIG. 1 shows a preparative process of a bifunctional nucleoside hydrogel according to the present invention.

2. The Preparative Process of the Bifunctional Nucleoside Hydrogel According to the Present Invention is Shown in FIG. 1.

Example 1 Preparation of the Bifunctional Nucleoside Hydrogel According to the Present Invention Isoguanosine (isoG) and NaB(OH)$_4$ at a molar ratio of 1:1 were dissolved in ultrapure water, and heated to fully dissolve and obtain a clear and transparent solution. The concentration of isoguanosine in the resultant solution was 1.4 wt %. Then, guanosine (G) was added to the solution, and the molar ratio of guanosine and isoguanosine was 1:1, that is, the concentration of guanosine was 1.4 wt %. The mixture was heated to full dissolution, and the transparent and colorless isoGBG hydrogel was obtained after naturally cooling at room temperature, i.e. the dual functional nucleoside hydrogel of the present invention, in which the concentration of isoGBG hydrogel was 14000 μg/ml.

By the preparative method of Example 1, isoGBG hydrogels at different concentrations could be obtained only by changing the concentrations of isosguanosine and guanosine in the solution (Embodiments 2-10).

Example 2 Preparation of the Bifunctional Nucleoside Hydrogel According to the Present Invention The concentration of isoguanosine and guanosine in the solution was 0.8 wt %, and the isoGBG hydrogel at a concentration of 8000 μg/ml was prepared.

Example 3 Preparation of the Bifunctional Nucleoside Hydrogel According to the Present Invention The concentration of isoguanosine and guanosine in the solution was 0.08 wt %, and the isoGBG hydrogel at a concentration of 800 μg/ml was prepared.

Example 4 Preparation of the Bifunctional Nucleoside Hydrogel According to the Present Invention The concentration of isoguanosine and guanosine in the solution was 0.04 wt %, and the isoGBG hydrogel at a concentration of 400 μg/ml was prepared.

Example 5 Preparation of the Bifunctional Nucleoside Hydrogel According to the Present Invention The concentration of isoguanosine and guanosine in the solution was 0.02 wt %, and the isoGBG hydrogel at a concentration of 200 μg/ml was prepared.

Example 6 Preparation of the Bifunctional Nucleoside Hydrogel According to the Present Invention The concentration of isoguanosine and guanosine in the solution was 0.01 wt %, and the isoGBG hydrogel at a concentration of 100 μg/ml was prepared.

Example 7 Preparation of the Bifunctional Nucleoside Hydrogel According to the Present Invention The concentration of isoguanosine and guanosine in the solution was 0.0075 wt %, and the isoGBG hydrogel at a concentration of 75 μg/ml was prepared.

Example 8 Preparation of the Bifunctional Nucleoside Hydrogel According to the Present Invention The concentration of isoguanosine and guanosine in the solution was 0.005 wt %, and the isoGBG hydrogel at a concentration of 50 μg/ml was prepared.

Example 9 Preparation of the Bifunctional Nucleoside Hydrogel According to the Present Invention The concentration of isoguanosine and guanosine in the solution was 0.5 wt %, and the isoGBG hydrogel at a concentration of 5000 μg/ml was prepared.

Example 10 Preparation of the Bifunctional Nucleoside Hydrogel According to the Present Invention The concentration of isoguanosine and guanosine in the solution was 1.0 wt %, and the isoGBG hydrogel at a concentration of 10000 μg/ml was prepared.

By the preparative method of Example 1, the bifunctional nucleoside hydrogel of the present invention can also be obtained by changing the type of borate in the solution (The borate in Example 1 being NaB(OH)$_4$) (Examples 11-14).

Example 11 Preparation of the Bifunctional Nucleoside Hydrogel According to the Present Invention NaB(OH)$_4$ in Example 1 was substituted by LiB(OH)$_4$, to prepare the bifunctional nucleoside hydrogel of the present invention.

Example 12 Preparation of the Bifunctional Nucleoside Hydrogel According to the Present Invention NaB(OH)$_4$ in Example 1 was substituted by KB(OH)$_4$, to prepare the bifunctional nucleoside hydrogel of the present invention.

Example 13 Preparation of the Bifunctional Nucleoside Hydrogel According to the Present Invention NaB(OH)$_4$ in Example 1 was substituted by RbB(OH)$_4$, to prepare the bifunctional nucleoside hydrogel of the present invention.

Example 14 Preparation of the Bifunctional Nucleoside Hydrogel According to the Present Invention NaB(OH)$_4$ in Example 1 was substituted by CsB(OH)$_4$, to prepare the bifunctional nucleoside hydrogel of the present invention.

Other nucleosides were used to prepare hydrogels by the present inventor, and the experimental results indicated that other nucleosides were unable to form hydrogels.

Comparative Example 1 Preparation of isoG Hydrogel

Isoguanosine (isoG) and NaB(OH)$_4$ at a molar ratio of 1:1 were dissolved in PBS, and heated to fully dissolve and obtain a clear and transparent solution. The concentration of isoguanosine in the resultant solution was 0.5 wt %, and then the solution was gradually cooled at room temperature, to obtain isoG hydrogel at a concentration of 5 mg/ml.

Comparative Example 2 Preparation of isoG Hydrogel

Isoguanosine (isoG) and NaB(OH)$_4$ at a molar ratio of 1:1 were dissolved in PBS, and heated to fully dissolve and obtain a clear and transparent solution. The concentration of isoguanosine in the resultant solution was 1.0 wt %, and then the solution was gradually cooled at room temperature, to obtain isoG hydrogel at a concentration of 10 mg/ml.

The beneficial effects of the present invention are illustrated by following specific experimental examples.

Experimental Example 1 Confirmation of the Molecular Structure of Bifunctional Nucleoside Hydrogels

1. Experimental Method

Nuclear magnetic resonance $^{11}$B NMR and $^1$H NMR, as well as infrared spectra were used to determine the structure of isoGBG hydrogel according to the present invention.

2. Experimental Results

Figure 2:
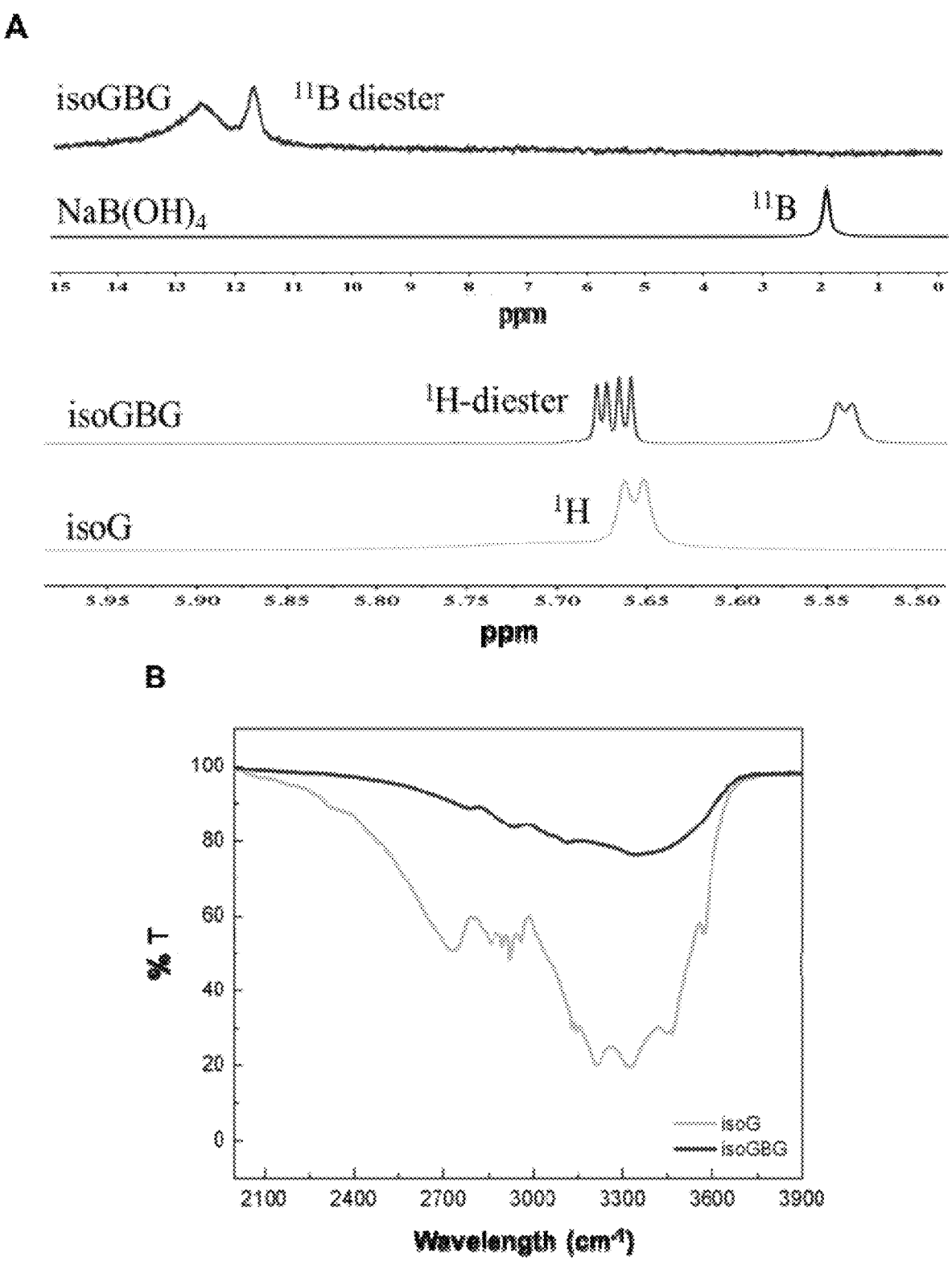
FIG. 2 is the confirmation of the chemical structure of isoGBG hydrogel. Panel A: The $^{11}B$ NMR spectra of NaB$(OH)_4$ and isoGBG, and the $^1H$ NMR spectra of isoG and isoGBG in DMSO; panel B: The IR spectra of isoG and isoGBG; panel C and panel D: VT $^{11}B$ NMR and VT $^1H$ NMR spectra of isoGBG in $D_2O$ during the temperature change from 25° C. to 65° C.
Figure 2:
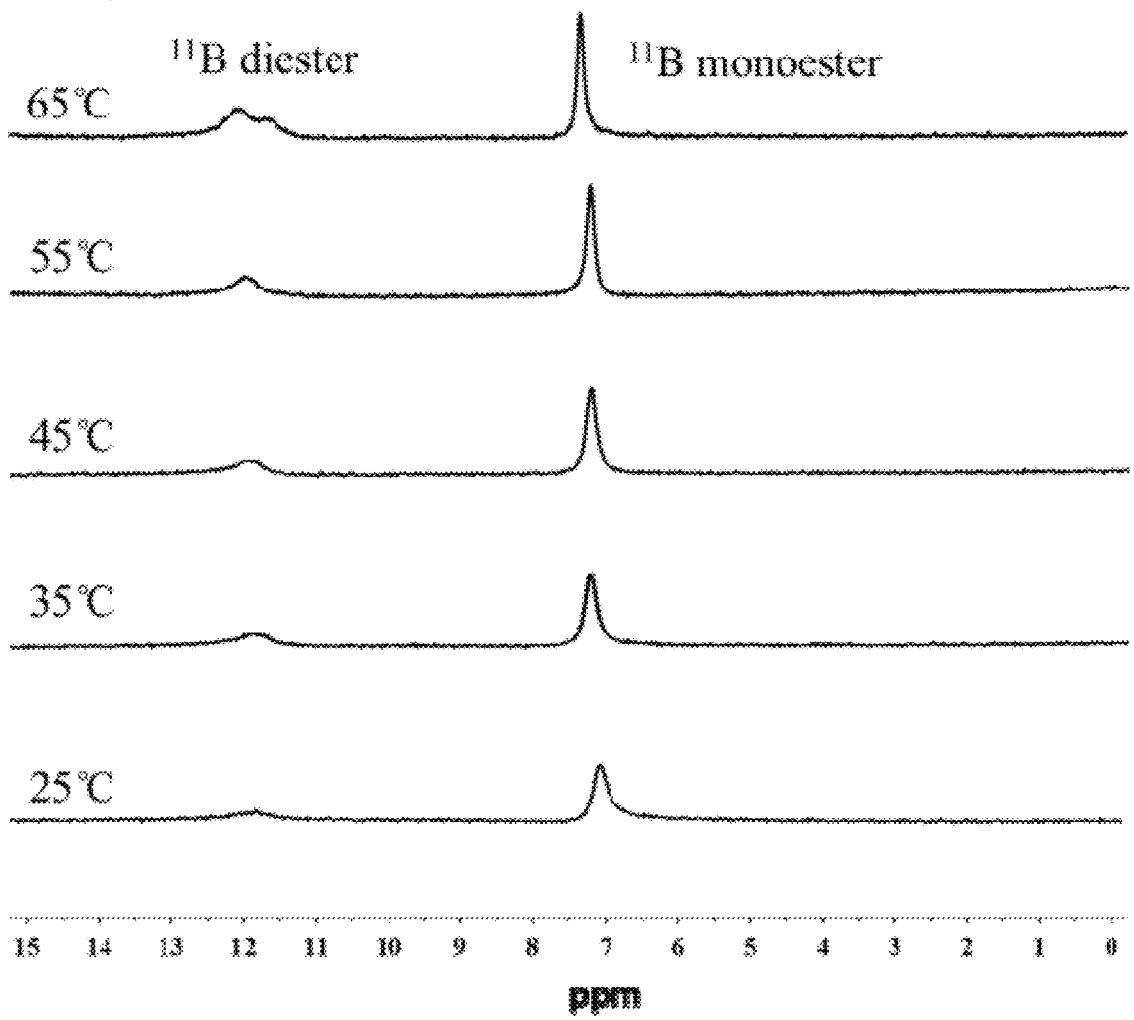
Figure 2:
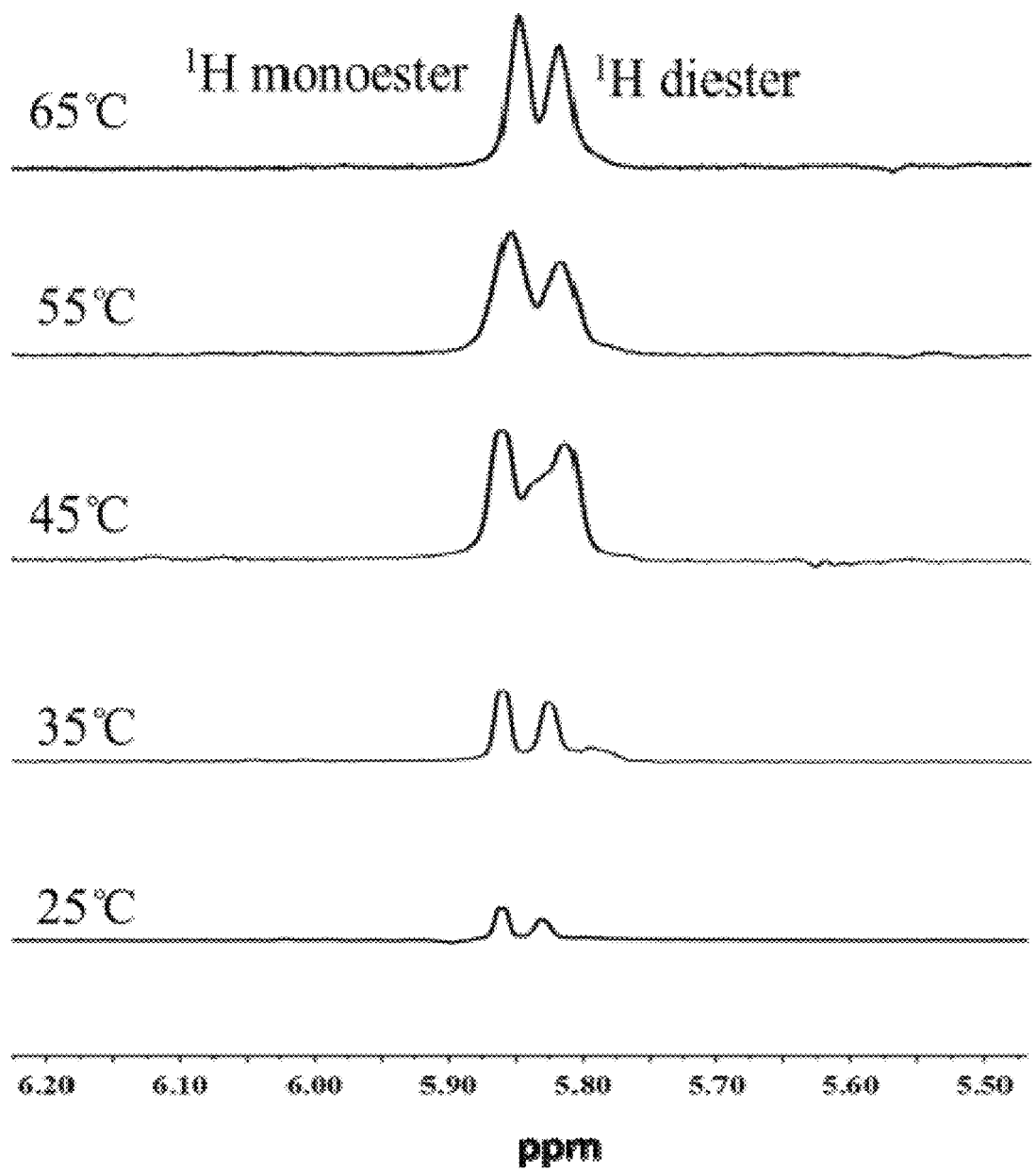

To confirm the structure and properties of isoGBG hydrogel, nuclear magnetic resonance $^{11}$B NMR and $^1$H NMR, as well as infrared spectra were used to elucidate the chemical structure thereof, and the experimental results indicated that there were boric acid diester bond in isoGBG hydrogel (as shown in FIG. 2).

Experimental Example 2 Study on the In Vitro Anti-Tumor Activity of the Bifunctional Nucleoside Hydrogel According to the Present Invention

1. Experimental Method

In this experiment, the effects of isoGBG hydrogel (isoGBG hydrogel prepared in Examples 3-8 of the present invention) at different concentrations (50, 75, 100, 200, 400, 800 μg/ml) on human lung cancer cell A549, glioma cell U251, osteoma cell U2OS, colon cancer cell HCT-116, breast cancer cell MCF-7, oral squamous cell carcinoma cell HSC-3 and tongue squamous cell carcinoma cell UM1 were detected by CCK8 assay. In the control group, NaB(OH)$_4$ ultrapure aqueous solution without isoguanosine and guanosine was administrated (i.e. the concentration of isoGBG hydrogel being 0 μg/ml), and the concentration of NaB(OH)$_4$ in ultrapure aqueous solution was the same as that in Example 3, while in the blank control group, PBS solution was used.

The specific operation process was as follows:
(1) Well-growing A549, U251, U2OS, HCT-116, MCF-7, HSC-3, and UM1 cells were respectively collected to prepare cell suspensions. After the cell density was adjusted, the cells were inoculated in 96-well plates, and the plates were incubated in a 37° C., 5% CO$_2$ cell incubator;
(2) After cultivating for 4-6 h, when the cells adhered to the wall, 100 μl isoGBG hydrogels of different concentrations prepared in Example 3-8 (isoGBG hydrogel was a supramolecular hydrogel, and when the shear stress was given under injection conditions, the gel could become a liquid state, while after removing the shear stress, it would return to the gel state immediately), NaB(OH)$_4$ solution of the control group, and PBS solution of the blank control group were respectively added, and the plates were placed in the incubator and incubated for further 24 h;
(3) After 24 h incubation, CCK8 reagent was used to detect cell viability. 96-well plates were taken out, the medium was removed, and then 10% CCK8 reagent was added. The absorbance (OD) at 450 nm wavelength was detected by a microplate reader. Each group was designed to have ≥3 multiple holes, and the results are averaged. The experiment was independently repeated 3 times. Percentage of cell viability (%)=experimental group (OD)/control group (OD)×100%.

2. Experimental Results

Figure 3:
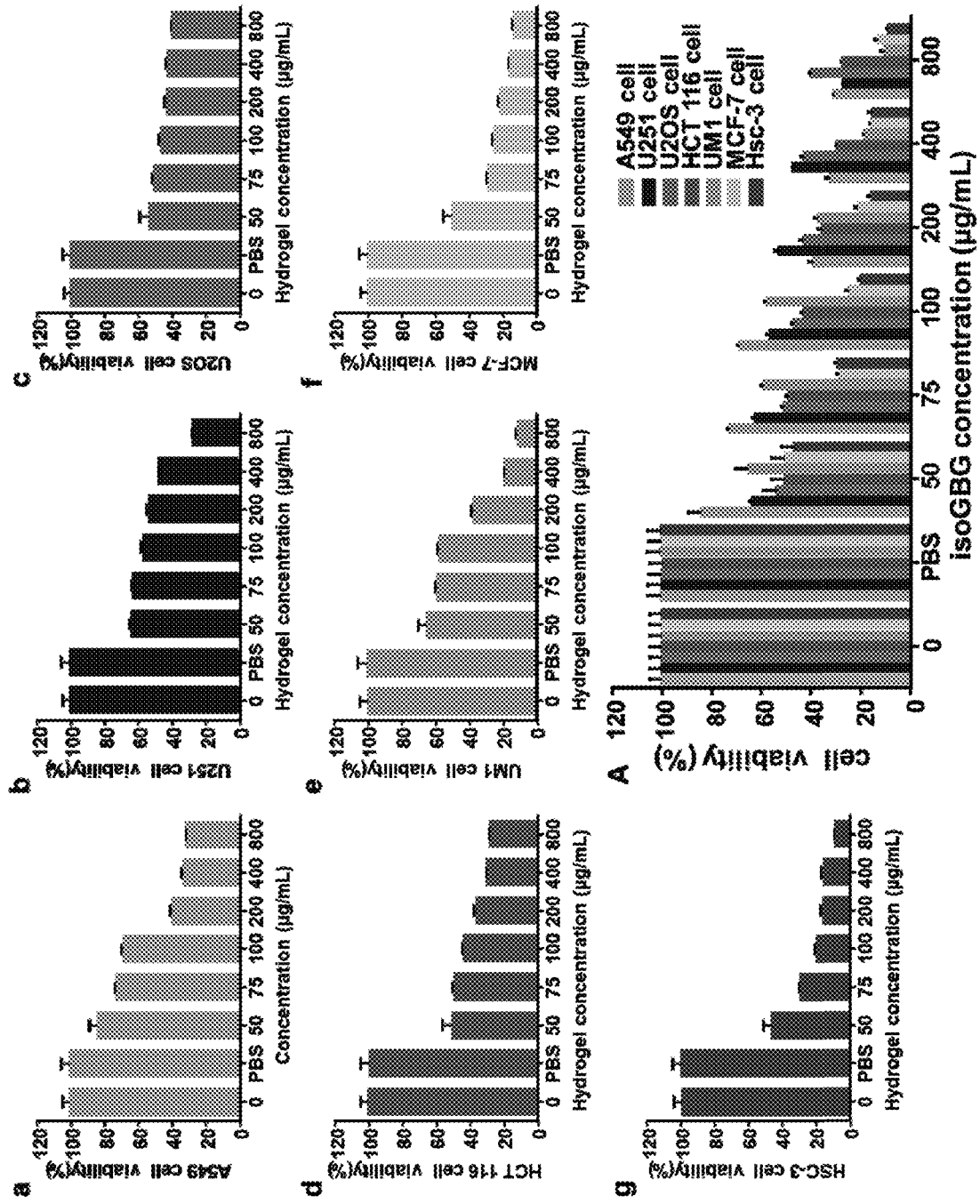
FIG. 3 shows the effect of isoGBG hydrogel on the activity of A549, U251, U2OS, HCT-116, MCF-7, HSC-3 and UM1 malignant tumor cells detected by CCK8.

The effect of isoGBG hydrogel according to the present invention on the activity of A549, U251, U2OS, HCT-116, MCF-7, HSC-3 and UM1 malignant tumor cells was shown in FIG. 3. As shown in FIG. 3, isoGBG hydrogel had an inhibitory effect on the above-mentioned tumor cells, indicating that isoGBG hydrogel has anti-tumor activity on the above-mentioned tumor cells, and as the concentration of isoGBG hydrogel (0 μg/mL-800 μg/mL) increased, the anti-tumor activity became strong accordingly. Among them, isoGBG had the strongest inhibitory effect on oral squamous cell carcinoma cells, and the cytostatic activity could be as high as 90%. The experimental results indicated that isoGBG hydrogel had certain in vitro anti-tumor activity against lung cancer, glioma, osteoma, colon cancer, breast cancer, oral squamous cell carcinoma, tongue squamous cell carcinoma, and other common clinical malignancies, as well as had potential application prospects. Among them, isoGBG hydrogel had the best in vitro anti-tumor activity against oral squamous cell carcinoma.

Experimental Example 3 the Bifunctional Nucleoside Hydrogel of the Present Invention Inhibiting the Growth of Transplanted Tumor of Oral Squamous Cell Carcinoma HSC-3

1. Experimental Method

In order to investigate the effect of isoGBG hydrogel on the growth of transplanted tumor of oral squamous cell carcinoma HSC-3, an HSC-3 nude mouse xenograft model was established: the oral squamous cell carcinoma HSC-3 cells in logarithmic growth phase were collected, and serum-free medium DMEM was used to wash the cells 3 times, then the cells were resuspended and counted. The cell concentration was adjusted to $2 \times 10^7$ cell/ml, and 100 μl cell suspension was subcutaneously inoculated on the right flank of nude mice, to construct an oral squamous cell carcinoma HSC-3 xenograft tumor model. 5 days after inoculation of oral squamous cell carcinoma HSC-3 cells, tumor nodules could be seen with naked eyes, and subcutaneous masses could be palpated.

The modeled nude mice were randomly divided into groups (n=10 mice/group), PBS solution was used as the blank control group (PBS group), while isoG hydrogel prepared in Comparative Examples 1 and 2 (isoG hydrogel group) and isoGBG hydrogel prepared in Examples 9 and 10 (isoGBG hydrogel group) were used in the test groups. Corresponding treatments were carried out in each group by peritumoral injection, once a week, and 100 μl injection volume was each used for 3 weeks. The hydrogel concentrations of Example 9 and Comparative Example 1 were 25 mg·kg$^{-1}$ after being injected into nude mice, while the hydrogel concentrations of Example 10 and Comparative Example 2 were 50 mg·kg$^{-1}$ after being injected into nude mice. The tumor volume was measured with a sterile vernier caliper every 3-4 days, and the weight of mice was weighed. Meanwhile, whether the nude mice's hair, behavior, and weight were abnormal was observed. The calculation formula of tumor volume was: tumor volume $(V) = \pi/6 \times$ the maximum diameter $\times$ (the minimum diameter). The results were expressed as mean±standard error. The tumor inhibition rate was the tumor volume ratio of the test group and the blank control group.

21 days after the first administration, the therapeutic effect of isoGBG hydrogel on HSC-3 nude mice transplanted tumor subcutaneous model was investigated.

2. Experimental Results

Figure 4:
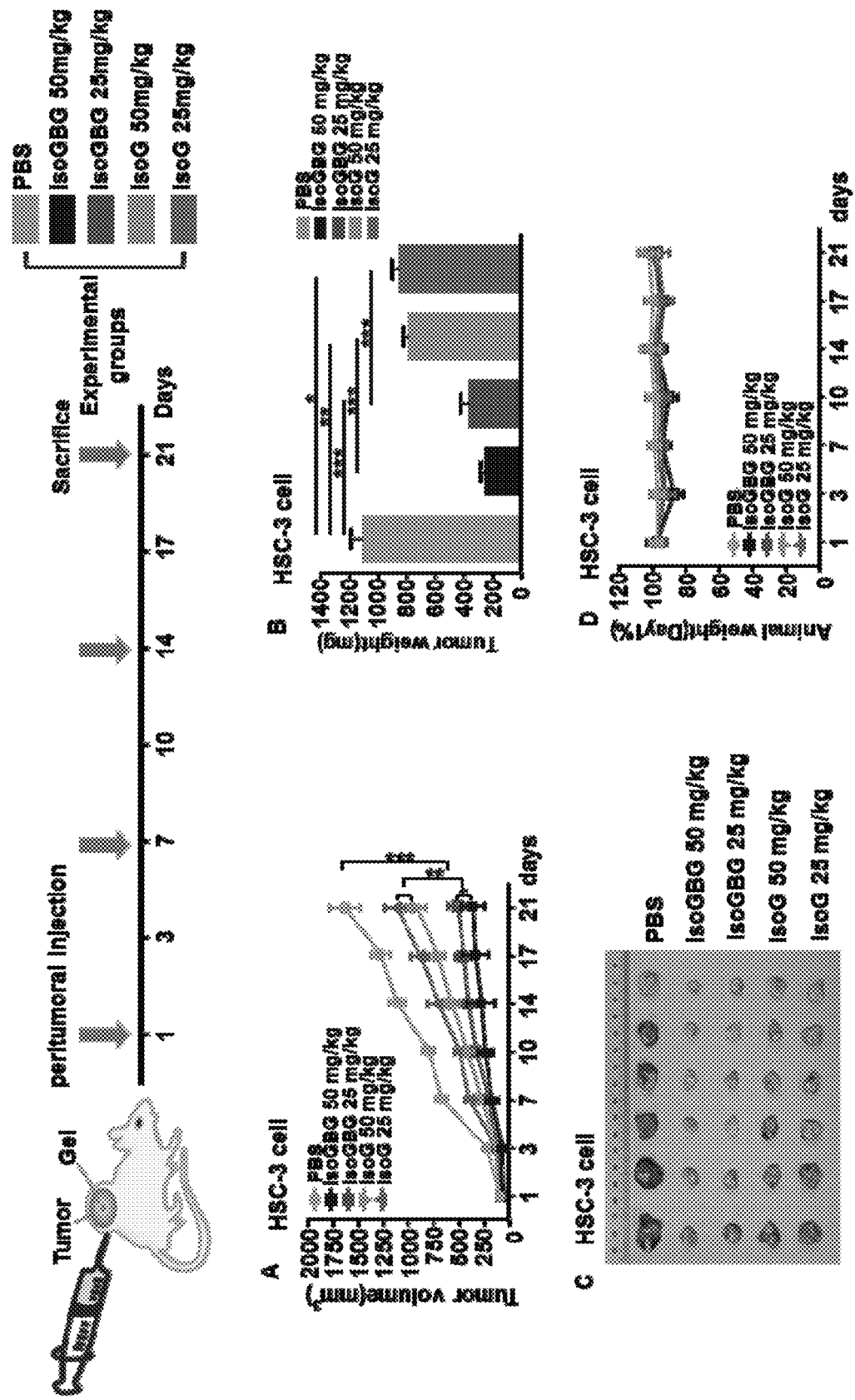
FIG. 4 shows that IsoGBG hydrogel inhibits the growth of oral squamous cell carcinoma HSC-3 xenograft in nude mice by peritumoral administration. A) Growth curve of HSC-3 tumor in each treatment group; B) On the $21^{st}$ day, the weight of HSC-3 transplanted tumor in nude mice of each treatment group decreased; C) On the 21$^{st}$ day, the visual images of tumors in each group; D) Weight change curve of each treatment group; (*) P<0.05, () P<0.01, (*) P<0.001, n=10.

The effect of isoGBG hydrogel on the growth of transplanted tumor of oral squamous cell carcinoma HSC-3 was shown in FIG. 4. As shown in FIG. 4, the inhibition ratio of isoGBG hydrogel at a concentration of 5 mg/ml on the growth of transplanted tumors was about 69.10%, and its inhibition on the growth of transplanted tumors was significantly better than that of PBS group and isoG hydrogel group; while as the concentration of isoGBG hydrogel was increased to 10 mg/ml, the tumor inhibition rate of isoGBG hydrogel was better, which was significantly improved to 78.80%. At the same time, as shown in FIG. 4, after isoGBG hydrogel was used to treat oral squamous cell carcinoma xenografts, the tumor volume was significantly reduced and was concentration-dependent. As the concentration of the hydrogel increased, its curative effect of inhibiting tumor growth was more obvious ($P<0.05$), and better than that of PBS group and isoG hydrogel group. Therefore, it could be found that isoGBG hydrogel, as a dual-functional hydrogel having carrier and therapeutic effects, could inhibit the growth of oral squamous cell carcinoma xenografts in vivo, which might provide a new approach for the treatment of oral squamous cell carcinoma.

In summary, the bifunctional nucleoside hydrogel of the present invention had both carrier and medicinal effects, as well as obvious inhibition on the activity of tumor cells, especially for lung cancer, glioma, bone tumor, colon cancer, breast cancer, oral squamous cell carcinoma, and tongue squamous cell carcinoma. Among them, the inhibition effect on the activity of oral squamous carcinoma cells was the best. In addition, the bifunctional nucleoside hydrogel of the present invention could inhibit the growth of transplanted tumor of oral squamous cell carcinoma HSC-3 cell lines in vivo. Therefore, the bifunctional nucleoside hydrogel had potential application prospect in the preparation of antitumor drugs. Especially, it could provide a new way for the treatment of oral squamous cell carcinoma.

The invention claimed is:

1. A bifunctional nucleoside hydrogel comprising cross-linked isoguanosine, guanosine, and borate, wherein said hydrogel is formed by cross-linking of isoguanosine, guanosine and borate in water or in an aqueous solution.

2. The bifunctional nucleoside hydrogel according to claim 1, wherein a molar ratio of isoguanosine, guanosine, and borate is 1:(1-5):(1-5).

3. The bifunctional nucleoside hydrogel according to claim 1, wherein the aqueous solution that is obtained by dissolving isoguanosine, guanosine and borate in water or in the aqueous solution, and the concentration of isoguanosine is 0.005-5.6 wt %.

4. The bifunctional nucleoside hydrogel according to claim 1, wherein said borate is selected from $LiB(OH)_4$, $NaB(OH)_4$, $KB(OH)_4$, $RbB(OH)_4$, $CsB(OH)_4$ and mixtures thereof.

5. The bifunctional nucleoside hydrogel according to claim 1, wherein said aqueous solution is a phosphate buffer.

6. The bifunctional nucleoside hydrogel according to claim 1, wherein said cross-linking comprising dissolving isoguanosine, guanosine, and borate in hot water or the aqueous solution, followed by cooling and cross-linking.

7. The bifunctional nucleoside hydrogel according to claim 6, wherein the cross-linking occurs at room temperature.

8. A preparative method of the bifunctional nucleoside hydrogel according to claim 1, comprising:
dissolving isoguanosine, guanosine and borate in water or the aqueous solution under heating, and then cooled and crosslinked.

9. The preparative method according to claim 8, wherein isoguanosine and borate are dissolved in water or the aqueous solution under heating to form a first mixture, and is dissolved in the mixture under heating to form a second mixture, and the second mixture is gradually cooled at room temperature and crosslinks.

10. A method for treating a tumor, comprising applying an antitumor drug comprising a bifunctional nucleoside hydrogel comprising cross-linked isoguanosine, guanosine, and borate to a subject in need thereof,
wherein the tumor is selected from lung cancer, glioma, osteoma, colon cancer, breast cancer, oral squamous cell carcinoma, and tongue squamous cell carcinoma, and
wherein the bifunctional nucleoside hydrogel is formed by cross-linking of isoguanosine, guanosine and a borate selected from $LiB(OH)_4$, $NaB(OH)_4$, $KB(OH)_4$, $RbB(OH)_4$, $CsB(OH)_4$, and mixtures thereof.

11. The method according to claim 10, wherein a molar ratio of isoguanosine, guanosine, and borate of the bifunctional nucleoside hydrogel is 1:(1-5):(1-5).

12. The method according to claim 11, wherein the molar ratio of isoguanosine, guaniosine, and borate is 1:1:1.

13. The method according to claim 10, wherein the bifunctional nucleoside hydrogel is prepared by a preparation method comprising:
dissolving isoguanosine, guanosine, and the borate in water or in an aqueous solution at an elevated temperature to form a reaction mixture; and
cooling the reaction mixture.

14. The method according to claim 13, wherein the reaction mixture comprises 0.005-5.6 wt % of isoguanosine.

15. The method according to claim 14, wherein the reaction mixture comprises 0.3-5.6 wt % of isoguanosine.

16. The method according to claim 13, wherein the aqueous solution is a phosphate buffer.

17. The method according to claim 10, wherein the tumor is oral squamous cell carcinoma or tongue squamous cell carcinoma.

* * * * *